US009947201B2

(12) United States Patent
Johnson et al.

(10) Patent No.: US 9,947,201 B2
(45) Date of Patent: Apr. 17, 2018

(54) ASSISTANCE WITH SETTING CLINICAL ALARM LIMITS

(71) Applicant: KONINKLIJKE PHILIPS N.V., Eindhoven (NL)

(72) Inventors: Soren Steiny Johnson, Lynnfield, MA (US); Elizabeth J. Zengo, Newbury, NH (US); George Thissell, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/108,801

(22) PCT Filed: Dec. 18, 2014

(86) PCT No.: PCT/IB2014/067078
§ 371 (c)(1),
(2) Date: Jun. 29, 2016

(87) PCT Pub. No.: WO2015/101891
PCT Pub. Date: Jul. 9, 2015

(65) Prior Publication Data
US 2016/0321904 A1  Nov. 3, 2016

Related U.S. Application Data

(60) Provisional application No. 61/923,789, filed on Jan. 6, 2014.

(51) Int. Cl.
*G08B 21/04*  (2006.01)
*G06F 19/00*  (2011.01)

(52) U.S. Cl.
CPC ..... *G08B 21/0453* (2013.01); *G06F 19/3406* (2013.01); *G06F 19/3418* (2013.01)

(58) Field of Classification Search
CPC ............. G06F 19/3406; G06F 19/3418; G06F 19/3487; G08B 21/0453; A61B 5/044; A61B 5/0452; A61B 5/743; G01D 7/04
See application file for complete search history.

(56) References Cited

U.S. PATENT DOCUMENTS

| | | | |
|---|---|---|---|
| 2003/0013978 A1* | 1/2003 | Schlegel | A61B 5/044 600/509 |
| 2003/0018241 A1 | 1/2003 | Mannheimer | |
| 2004/0236187 A1 | 11/2004 | Bock | |
| 2005/0246366 A1* | 11/2005 | Kouchi | A61B 5/044 |
| 2006/0220885 A1 | 10/2006 | Bock | |

(Continued)

OTHER PUBLICATIONS

"Top 10 Health Technology Hazards for 2013", Nov. 2012 ECRI Institute.

*Primary Examiner* — Sisay Yacob

(57) ABSTRACT

A medical monitoring system includes one or more processors (23) configured to receive (84) monitored physiological measures (16) and corresponding one or more alarm occurrences for a patient (10) and an adjustable alarm setting (56). The one or more processors are further configured to configure (86) a display (28) of at least one monitored physiological measure (76) and a retrospective graphical illustration of the physiological measure (30) including illustrations of the one or more occurrences of alarms (32) corresponding to the adjustable alarm setting (56).

14 Claims, 3 Drawing Sheets

(56) References Cited

U.S. PATENT DOCUMENTS

Figure 1:
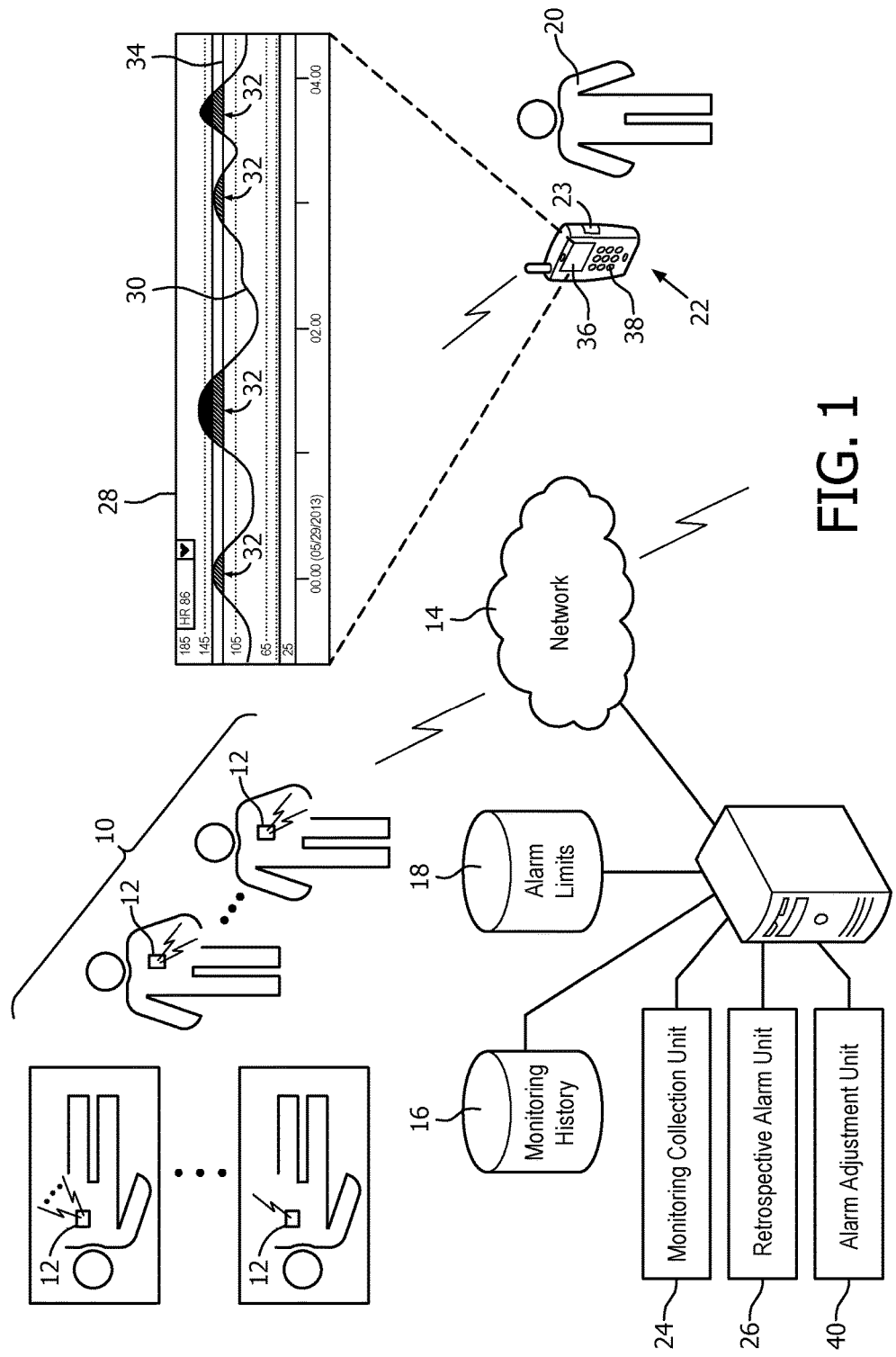

| | | |
|---|---|---|
| 2009/0247851 A1 | 10/2009 | Batchelder |
| 2010/0238192 A1* | 9/2010 | Kouchi ................. A61B 5/044 |
| | | 345/593 |
| 2011/0001605 A1* | 1/2011 | Kiani ................... G06F 19/327 |
| | | 340/5.6 |
| 2011/0118573 A1 | 5/2011 | McKenna |
| 2012/0116194 A1 | 5/2012 | Gross |
| 2013/0044111 A1 | 2/2013 | Vangilder |
| 2013/0045685 A1 | 2/2013 | Kiani |
| 2013/0162433 A1* | 6/2013 | Muhsin ............. G06F 17/30516 |
| | | 340/573.1 |
| 2013/0211214 A1* | 8/2013 | Olsen .................... A61B 5/742 |
| | | 600/316 |

* cited by examiner

ASSISTANCE WITH SETTING CLINICAL ALARM LIMITS

CROSS REFERENCE TO RELATED APPLICATIONS

This application is the U.S. National Phase application under 35 U.S.C. § 371 of International Application No. PCT/IB2014/067078, filed Dec. 18, 2014, published as WO 2015/101891 on Jul. 9, 2015, which claims the benefit of U.S. Provisional Patent Application No. 61/923,789 filed Jan. 6, 2014. These applications are hereby incorporated by reference herein.

The following relates generally to patient monitoring. It finds particular application in conjunction with physiological measurement alarms of patients, and will be described with particular reference thereto. However, it will be understood that it also finds application in other usage scenarios and is not necessarily limited to the aforementioned application.

Patient monitoring involves devices which monitor vital signs of patients. Physiological measurements are generated by the monitoring devices and typically sent to a monitoring system. The monitoring system receives the physiological measures and can generate alarms to a healthcare practitioner based on ranges or threshold values indicative of a medical concern. For example, a heart rate above a predetermined value or below a second predetermine value can indicate a cause for concern. The alarm settings are typically based on one or more studies of the patient population, accepted medical practice, local site policies, and/or healthcare practitioner experience. However, patient conditions are quite variable and the result often is a large number of alarm conditions.

The number of alarm conditions has created an issue known as "alarm fatigue" in the healthcare profession. Healthcare practitioners or caregivers are inundated with monitoring alarms. A healthcare practitioner such as a nurse or a physician is often responsible for a group of monitored patients. The number of measurements and the number of patients can vary with the patient conditions. For example, more acute patients typically have more physiological measurements or vital signs being taken. Some healthcare organizations have a baseline number of patient physiological measures such as an ECG and/or $SpO_2$ and add other measures for more acute patients such as ST maps. A single patient may have 3, 4, or more physiological measures with each having multiple parameters which can cause an alarm to be generated to the healthcare practitioner. With a group of monitored patients, the number of alerts that can be generated can overwhelm the ability of the healthcare practitioner(s) to effectively review, discard, or act on the generated alarms. Alarms are critical to patient safety and processing alarms can be time consuming and lead to missed alarms or delayed responses and, in some instances, ignored alarms. In addition, many of the alarms are unnecessary or false alarms based on the patient condition and/or patient history. Moreover, with portable communication devices, the alarms follow a mobile healthcare practitioner.

Tailoring alarm limits to each patient can reduce alarms, but tailoring the limits can itself be time consuming. The alarm limit for an individual measurement can be reset after careful consideration by the healthcare practitioner. However, careful consideration typically involves remembering which alarm was set for a particular patient when, identifying the parameter which generated the alarm, and adjusting the one setting. Often the resetting of an alarm limit occurs from an alarm condition which is clearly repetitive and unnecessary, and the other alarms continue with existing settings. This approach means the most egregious of the limits are addressed, but the overall number of alarms remains unnecessarily high which continues to contribute to the alarm fatigue. Each work shift of caregivers can begin the process again as patient conditions change over time with the overall result of continued alarm fatigue.

Software tools exist which show the current settings and current monitored vital sign which provide only a confirmation of the limits pertaining to a monitored vital sign. On some monitors, such as with central monitors, some vital signs are shown numerically and some in waveforms. The healthcare practitioner is left to identify each source of unnecessary alarms and the corresponding monitored vital sign in order to review and revise the setting. Practitioners can find themselves in the situation of having to review a large quantity of messages sent as alarms to a mobile device a second time after patient care considerations are addressed to identify the sources or alarm limits of the unnecessary alarms.

The following discloses a new and improved assistance with setting clinical alarms which addresses the above referenced issues, and others.

In accordance with one aspect, a medical monitoring system includes one or more processors configured to receive monitored physiological measures and corresponding one or more alarm occurrences for a patient and an adjustable alarm setting. The one or more processors are further configured to configure a display of at least one monitored physiological measure and a retrospective graphical illustration of the physiological measure including illustrations of the one or more occurrences of alarms corresponding to the adjustable alarm setting.

In accordance with another aspect, a method of adjusting medical alarms includes receiving monitored physiological measures for a selected patient. A display of the monitored physiological measure, and a retrospective graphical illustration of the physiological measure including illustrations of the one or more occurrences of alarms corresponding to an adjustable alarm setting, is configured.

In accordance with another aspect, a medical monitoring system includes one or more processors and a display device. The one or more processors are programmed to receive at least one monitored physiological measure and corresponding one or more alarm occurrences for a selected patient, and configure a waveform display of the monitored physiological measure versus time, an alarm limit, and indicators of the corresponding one or more occurrences of alarms. The one or more processors are further programmed to receive input indicative of a change in the alarm limit, and change the alarm limit in the display. The display device is configured to display the configured waveform display.

One advantage is the reduction in clinically non-relevant alarms.

Another advantage resides in reducing alarm fatigue.

Another advantage resides in associating historical alarms with current alarm settings.

Another advantage resides in a workflow that supports timely and efficient healthcare practitioner review and assists in setting alarm limits at clinically relevant levels.

Another advantage resides in easily tailoring alarm settings to each patient.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of assistance with setting clinical alarms system.

Figure 2:
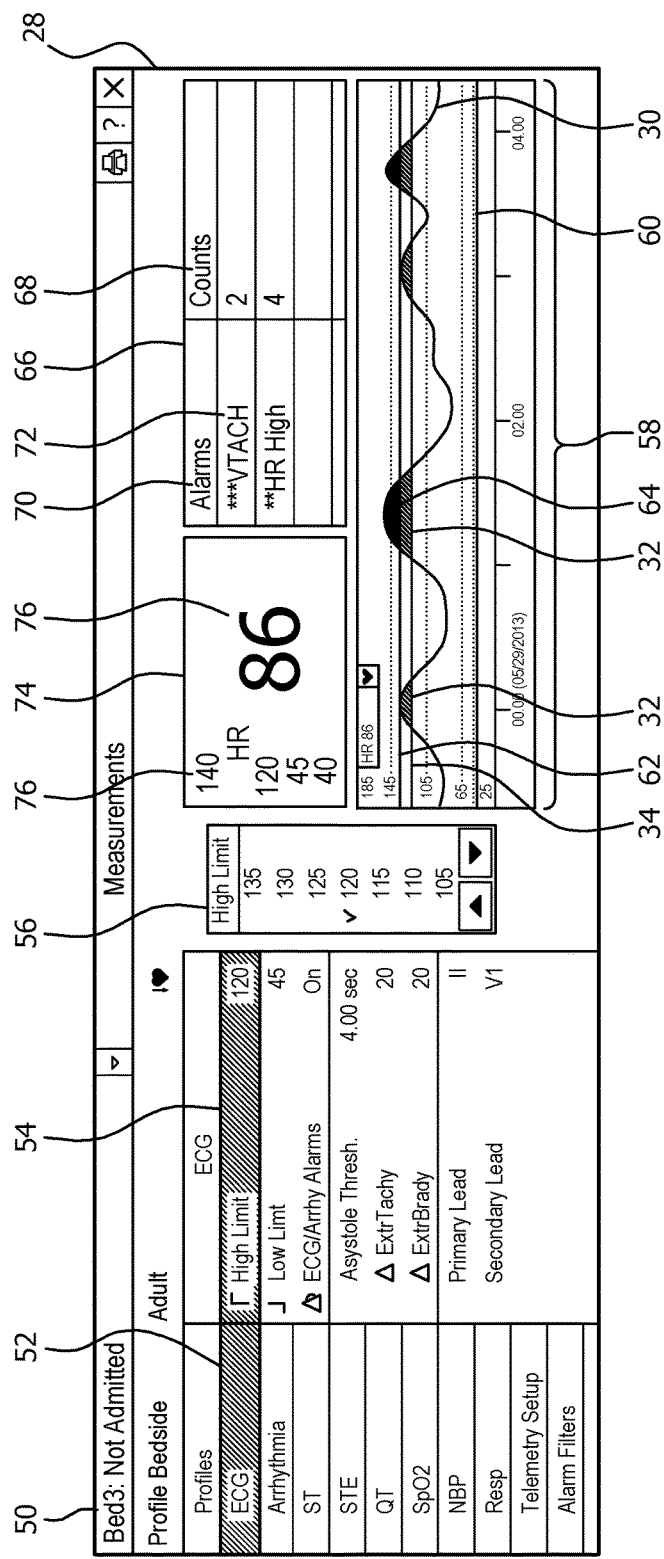

FIG. 2 illustrates an exemplary of a display that assists with setting clinical alarms.

Figure 3:
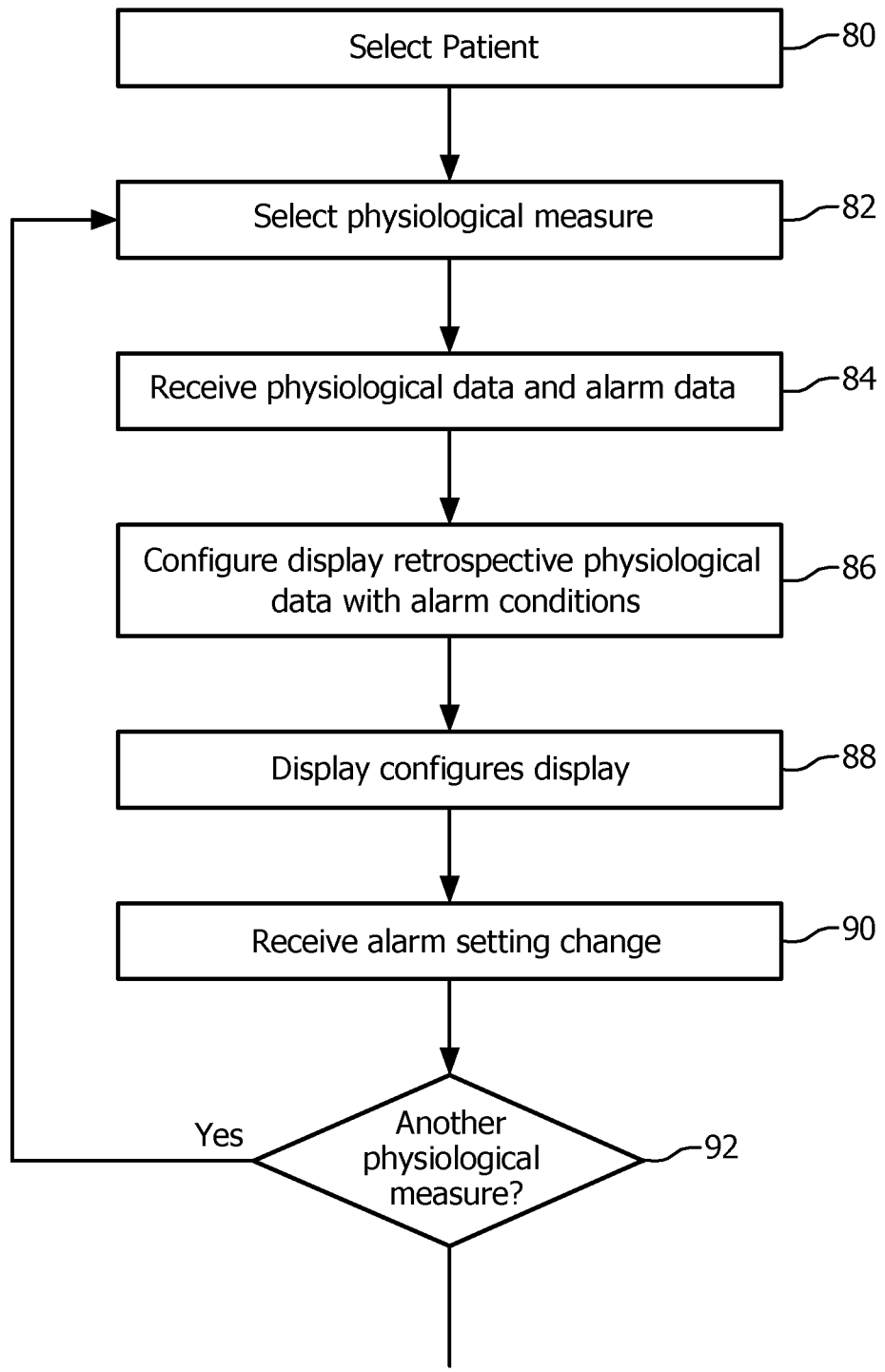

FIG. 3 flowcharts one method of using an embodiment of assisting with setting clinical alarms.

With reference to FIG. 1, an embodiment of a system which provides assistance with setting clinical alarms system is schematically illustrated. A medical monitoring system monitors the vital signs of one or more patients 10. The patients can be bed patients or ambulatory patients. The physiological parameters of each patient are monitored with at least one monitoring device 12 which measures and transmits physiological measures of patient vital signs, such as ECG, $SpO_2$, Arrhythmia, ST, STE, QT, NBP, RR, and the like. The monitoring devices 12 can transmit the physiological measures as raw data or as waveforms. The transmission can include wired or wireless transmission over a network 14. The network can include wireless and/or wired connections, and public and/or private connections.

The monitored physiological measures are stored in a data store of monitoring history 16 which includes the physiological measures and one or more occurrences of alarms according to set alarm limits 18. The monitoring history can include the raw data and/or processed waveforms, the time and duration of each alarm occurrence, and the alarm limit at the time of alarm occurrence. The alarm limits includes at least one adjustable alarm limit. For example, a heart rate (HR) alarm limit can include upper threshold values and lower threshold values for which an alarm is set. When the physiological measure is greater than the upper threshold value or lesser than the lower threshold value, an alarm occurs. The upper threshold value and lower threshold value for the HR physiological measures, for example, can be adjusted by a healthcare practitioner 20 using a computer device 22. A data store as used herein encompasses file systems and database systems and combinations. The database system can be relational, object oriented, and the like.

The healthcare practitioner 20, using the computer device 22 which includes one or more electronic processors 23, selects a patient and a monitored physiological parameter. A monitoring collection unit 24 receives from the monitoring history data store 16 the historical monitored physiological measure and corresponding historical alarm occurrences for the selected patient and alarm limit. The monitoring collection 24 receives from alarm limits data store 18 the corresponding alarm limits.

A retrospective alarm unit 26 configures a display 28 of the monitored physiological measures that includes a retrospective graphical illustration of the physiological measures versus time and occurrences of alarms corresponding to the adjustable alarm setting. By way of illustrative example, the graphical illustration of the physiological measures includes a waveform 30 or other graphical illustration of heart rate versus time for the preceding several hours. The waveform can retrieved from the data store and/or constructed from the stored raw data. The occurrences of alarms is illustrated graphically as part of the graphical illustration of the physiological measure with indicators 32 such as colored and/or shaded fill areas, bands, bars, etc. The configured display 28 includes an indicator of the alarm setting 34 such as a bolded and/or colored line extending parallel to a time axis, e.g. at the current high alarm limit for heart rate.

The configured display is displayed on a display device 36 to the reviewing healthcare practitioner. The display device 36 can be a display screen of the computer device 22 such as a mobile computer device or smartphone, PDA, tablet, laptop, desktop computer, and the like. The computer device can include a network-based server operatively connected to the computer device. The computer device can include one or more input devices 38 such as a touch screen, keypad, keyboard, mouse, microphone, and the like.

An alarm adjustment unit 40 receives an adjustment to the adjustable alarm setting and adjusts the adjustable alarm setting for the physiological measures of the selected patient. The adjustment is entered by the healthcare practitioner in response to the configured display 28 by the one or more input devices 38. In the illustrated embodiment, the healthcare practitioner adjusts the high alarm limit up or down. As the alarm limit is raised the occurrence and duration of alarms is decreased.

The various units or modules 24, 26, 40 are suitably embodied by an electronic data processing device, such as the one or more electronic processors of the computing device 22, or by a network-based server computer operatively connected with the computing device 22 by the network 14, by hardware or software modules, or so forth. The disclosed display configuration techniques are suitably implemented using a non-transitory storage medium storing instructions (e.g., software) readable by an electronic data processing device and executable by the electronic data processing device to perform the disclosed display configuration techniques.

A display device as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display and the like.

With reference to FIG. 2, an example of a configured display 28 that assists with setting clinical alarms is illustrated. Menus for a selected patient or bed 50 are shown. The healthcare practitioner selects a physiological measure or vital sign from a menu of vital signs 52. The healthcare practitioner can select an alarm limit such as a high limit from a menu of alarm limits 54. The healthcare practitioner can select and/or enter a new alarm limit setting 56. For example, the system can provide a list menu with clickable values such as shown or an entry box for entry of a selected value, radio button selection, and the like. The configured display 28 includes the waveform 30 representative of the monitored physiological measures versus time, i.e. the values of the patient's heart rate over the preceding 4 hours. In the embodiment of FIG. 2, the heat rate (HR) is as selected from the menu.

The waveform includes a timeline 58 of a predetermined historical period. The timeline can include a period of the current time and a preceding time interval, e.g. current time back to 4 hours previous, current time back to 6 hours previous, and the like. The timeline can be a prior work shift. The timeline can be selectable or configurable by the healthcare practitioner. For example, the waveform can be toggled between the current shift or most recent interval of vital signs and a comparable previous shift such the shift 16 hours previous based on 8 hour shift, or the values over the same period yesterday (24 hour period). Longer durations, such as several days or even weeks are also contemplated. The two intervals allow the healthcare practitioner to view how the patient is currently doing and how the patient did when the healthcare practitioner previously monitored the patient. Longer durations help the healthcare practitioner assess trends in the selected vital sign.

The configured display can include indicators of related alarm limits such as an indicator of a lower limit 60 and/or a limit computed as a function of an adjustable limit 62. For example, a ventricular tachycardia (VTACH) alarm limit can be computed as a function of the adjustable high HR limit, e.g. a computed 140 value for a VTACH limit of a 120 set HR alarm limit. Examples of indicators can include colored and/or shaded lines, or bars which indicate the alarm setting on the waveform graph. VTACH refers to a rapid heart beat that originates in the ventricles and is characterized by a missing p wave and an irregular QRS.

The alarm occurrences include indicators 32 of the time and duration of alarm occurrences relative to the waveform. The indicators can be specific to the type of alarm limit. For example, one indicator 32 can be for the adjustable alarm limit and a second indicator 64 can be for a function of the adjustable alarm limit, e.g. more severe patient acuity such as VTACH. The indicators 32, 64 can indicate a measure of patient acuity, e.g. yellow for less severe, red for most severe, and the like. The time and duration can be indicated as a colored or shaded fill of the waveform curve above or below the alarm limit indicator 34 or a colored or shaded portion of the region of the timeline 58 such as colored or shaded bars extending from the timeline. By viewing the waveform 30 and the alarm indicator 32 over time, the clinician can determine an appropriate limit setting. For example, if the trend shows improvement, e.g. fewer high HR occurrences, the alarm threshold can be lowered. If the trend shows that alarms occurrences are increasing, the threshold can be raised such that only the most significant events trigger an alarm.

The illustrated one or more alarm occurrences can include a tabular statistical display 66. The tabular statistical display includes one or more statistics of the alarm occurrences, such as a frequency or count 68 of the number of occurrences in a given or the predetermined interval, an average alarm occurrence time interval, mean time between alarm occurrences, etc. The tabular display can include related alarm occurrences, e.g. upper and/or lower limits, functions of the upper and/or lower limits, etc. The tabular statistical display of alarm occurrences can include indicators 72 of patient acuity, such as asterisks. The tabular statistical display can be sorted by patient acuity or a statistic such a frequency of occurrences, etc.

The configured display can include current numerics 74 or current numerical indicators. For example the current numerics 74 can include the current physiological measure 76. The current numerics can include one or more numerics of the current and related alarm settings 76, e.g. upper limit, lower limit, function of the upper limit, functions of lower limit, etc.

With reference to FIG. 3, one method of using an embodiment of assisting with setting clinical alarms is flowcharted. A patient or bed location of a patient is selected by a step or by a module 80. A physiological measure of the patient is selected by a step or by a module 82, such as ECG, SpO$_2$, Arrhythmia, ST, STE, QT, NBP, RR, and the like. The selections can be by menu such as described in reference to FIG. 2 with an input device such as a mouse or touch screen, or by voice commands using a microphone, etc.

By a step or by a module 84, the monitored physiological measures are received for a selected patient. The receiving can include retrieval of the waveforms, alarm occurrences, and alarm settings from the respective data stores for the predetermined time interval and/or work shift.

A display of the monitored physiological measures and a retrospective graphical illustration 28 of the physiological measures are configured including illustrations of the occurrences of alarms corresponding to an adjustable alarm setting by a step or by a module 86. The retrospective graphical illustration includes a waveform representative 30 of the monitored physiological measures. The alarm occurrences 32 include indicators of the time and duration of alarm occurrences relative to the waveform. The configured display can include an indicator 56 of the alarm setting. The alarm occurrences can include related alarm occurrences such as upper limits, lower limits, related physiological parameters, and/or functions of the upper or the lower limits.

The configured display 28 can include the illustrated alarm occurrences as a tabular statistical display including a frequency 68 of the alarm occurrences. The tabular statistical display can include alarm occurrences of related alarm settings corresponding to the physiological measures. The configured display can include indicators of patient acuity. For example, the indicators can be color filled areas 64 between the alarm limit indicator and the waveform and/or asterisks 72 in the tabular statistical display. By a step or by a module 88, the configured the configured is displayed on a display device.

An adjustment to the adjustable alarm setting for the physiological measures of the selected patient is received by a step or by a module 90. By a decision step or by a module 92, the steps can repeat for another physiological measure. The steps are performed by one or more programmed processors or electronic data processing devices of the computing device hardware modules such as ASICs, array processors, or the like, software modules, and the like. A non-transitory computer-readable storage medium carrying software controls the processors to perform the method.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A medical monitoring system, comprising:
   one or more processors configured to:
   receive monitored physiological measures and corresponding one or more alarm occurrences for a patient and an adjustable alarm setting; and
   configure a display of at least one monitored physiological measure and a retrospective graphical illustration of the physiological measure including illustrations of the one or more occurrences of alarms corresponding to the adjustable alarm setting, wherein the retrospective graphical illustration includes:
   a waveform representative of the monitored physiological measure versus time, wherein the waveform includes a timeline of a selected historical period,
   at least one alarm limit indicator drawn relative to the representative waveform, and
   indicators of the time and duration of the one or more occurrences of alarms drawn relative to the representative waveform.

2. The system according to claim 1, wherein the time and duration of the one or more occurrences of alarms are drawn relative to the representative waveform as a colored filled area between the at least one alarm limit indicator and the representative waveform.

3. The system according to claim 2, wherein the at least one alarm limit indicator includes a plurality of alarm limit indicators and the colored filled area includes a color indicative of patient acuity.

4. The system according to claim 1, wherein the one or more processors are further configured to:
   receive an adjustment to the adjustable alarm setting; and
   adjust the adjustable alarm setting for the physiological measures of the selected patient; and
   wherein the configured display adjusts the drawn at least one alarm limit indicator reflective of the adjusted alarm setting.

5. The system according to claim 1, wherein the illustrated one or more alarm occurrences are configured to display as tabular statistics which includes a frequency of the illustrated one or more alarm occurrences in a selected historical period and the configured display further includes a plurality of alarm settings corresponding to the physiological measure.

6. The system according to claim 1, wherein the display is further configured to include a drop down menu selection of the alarm setting.

7. The system according to claim 1, wherein the display is further configured to include a drop down menu selection of physiological measures.

8. A method of adjusting medical alarms, comprising:
   receiving monitored physiological measures for a selected patient; and
   configuring a display of the monitored physiological measure and a retrospective graphical illustration of the physiological measure including:
   a waveform representative of the monitored physiological measure versus time, wherein the waveform includes a timeline of a selected historical period,
   at least one alarm limit indicator drawn relative to the representative waveform and indicating an adjustable alarm setting, and
   at least one indicator of the time and duration of one or more occurrences of an alarm drawn relative to the representative waveform and illustrating the time and duration of the one or more occurrences of the alarm.

9. The method according to claim 8, wherein the time and duration of the alarm is indicated with a colored filled area between the at least one alarm limit indicator and the representative waveform.

10. The method, according to claim 8, further including:
    receiving an adjustment to the adjustable alarm setting; and
    adjusting the adjustable alarm setting for the physiological measures of the selected patient; and
    wherein the configuring display includes adjusting the drawn at least one alarm limit indicator reflective of the adjusted alarm setting.

11. The method according to claim 8, wherein configuring includes:
    configuring the illustrated one or more alarm occurrences as a tabular statistical display including a frequency of the one or more alarm occurrences, and the tabular statistical display includes one or more alarm occurrences of a plurality of alarm settings corresponding to the physiological measure.

12. A medical monitoring system comprising:
    a non-transitory computer-readable storage medium according to claim 8; and
    an electronic data processing device configured to read and execute the software carried by the non-transitory computer-readable storage medium.

13. The method according to claim 9, wherein the at least one alarm limit indicator includes a plurality of alarm limit indicators and the colored filled area includes a color indicative of patient acuity.

14. A non-transitory computer-readable storage medium carrying software which controls one or more electronic data processing devices to perform a method of adjusting medical alarms, the method comprising:
    receiving monitored physiological measures for a selected patient; and
    configuring a display of the monitored physiological measure and a retrospective graphical illustration of the physiological measure including:
    a waveform representative of the monitored physiological measure versus time, wherein the waveform includes a timeline of a selected historical period, at least one an alarm limit indicator drawn relative to the representative waveform and indicating an adjustable alarm setting, and at least one indicator of the time and duration of one or more occurrences of an alarm drawn relative to the representative waveform and illustrating the time and duration of the one or more occurrences of the alarm with a colored or shaded fill between the at least one alarm limit indicator and the representative waveform.

* * * * *